United States Patent [19]

Hentschel et al.

[11] Patent Number: 5,258,515
[45] Date of Patent: Nov. 2, 1993

[54] AQUEOUS SOLUTIONS OF SODIUM SALTS OF TRIMERCAPTO-S-TRIAZINE, THEIR PREPARATION AND USE

[75] Inventors: Klaus Hentschel, Rodenbach, Fed. Rep. of Germany; Marc Samson, Lokeren, Belgium; Marcel Vingerhoets, Brecht, Belgium; Karl-Ludwig Weber, Kapellen, Belgium

[73] Assignee: Degussa Aktiengesellschaft, Fed. Rep. of Germany

[21] Appl. No.: 932,745

[22] Filed: Aug. 25, 1992

Related U.S. Application Data

[63] Continuation of Ser. No. 569,137, Aug. 17, 1990, abandoned.

[30] Foreign Application Priority Data

Aug. 19, 1989 [DE] Fed. Rep. of Germany ....... 3927470

[51] Int. Cl.$^5$ .......................................... C07D 251/38
[52] U.S. Cl. .................................. 544/219; 544/180; 544/216
[58] Field of Search ......................................... 544/219

[56] References Cited

U.S. PATENT DOCUMENTS 3,778,368  12/1973  Nakamura et al. ................ 544/219

Primary Examiner—Mukund J. Shah
Assistant Examiner—Y. N. Gupta
Attorney, Agent, or Firm—Cushman, Darby & Cushman

[57] ABSTRACT

The invention relates to aqueous solutions of sodium salts of trimercapto-s-triazine whose molar saturation concentration at 0° C. to 40° C. is above the saturation concentration of trimercapto-s-triazine trisodium salt (TMT-Na$_3$). More than two but less than three hydrogen atoms of the trimercapto-s-triazine are replaced by sodium ions. The solutions preferably contain trimercapto-s-triazine disodium salt (TMT-Na$_2$) in addition to a little TMT-Na$_3$. Surprisingly, the water solubility of TMT-Na$_2$ is greater than that of TMT-Na$_3$. The solutions represent a suitable supply form for the active substance trimercapto-s-triazine (TMT-H$_3$) used in the separation of heavy metals The preparation takes place by means of reacting TMT-Na$_3$ with TMT-H$_3$ in a molar ratio of 1:greater than 0—less than 0.5, especially 1:0.1 to 1:<0.5 in aqueous solution.

7 Claims, No Drawings ns of sodium salts of trimercapto-s-triazine, their preparation and use

AQUEOUS SOLUTIONS OF SODIUM SALTS OF TRIMERCAPTO-S-TRIAZINE, THEIR PREPARATION AND USE

This is a continuation of application Ser. No. 07/569,137, filed on Aug. 17, 1990, which was abandoned.

The present invention relates to aqueous solutions of sodium salts of trimercapto-s-triazine whose molar saturation concentration at temperatures in a range of 0° C. to 40 °C is above that of trimercapto-s-triazine trisodium salt at a given temperature, their preparation and use.

BACKGROUND OF THE INVENTION

Trimercapto-s-triazine, (referred to as "TMT-$H_3$" in the following description) as well as sodium salts of this trivalent acid, have already been described by A. W. Hofmann - Chem. Ber. 18 (1885), 2196 –2207. TMT-$H_3$ was obtained by reacting 2,4,6-trichloro-s-triazine (cyanuric chloride) with sodium sulfide, followed by acidification. A monosodium salt of trimercapto-s-triazine was also isolated.

Nakamura et al. - Japan Kokai 49/1580 (Chem. Abstr. 81, 3972 b) prepared the monosodium salt of trimercapto-s-triazine (referred to as "TMT-Na" in the following description), in the form of the trihydrate.

According to the disclosure of Published German Patent Application DE-AS 22 40 549, heavy metals such as e.g. Cu, Cd, Ni, Hg, Ag, Pb can be separated as slightly soluble compounds from waste water using trimercapto-s-triazine or its water-soluble alkali-metal salts. TMT-Na is preferred in the exemplary comments of this document, the solubility in water of which is approximately 3% by weight; the di- and trisodium salt of trimercapto-s-triazine ("TMT-$Na_2$" and "TMT-$Na_3$", respectively, in the following description) are also suggested as possible precipitation reagents. The saturation concentration of aqueous solutions of alkali-metal-, ammonium- and alkaline-earth metal salts of mono-, di- and trimercapto-s-triazines is indicated to be in the range 0.01 to 25% by weight at 25° C. No information is provided in this document about the preparation of TMT-$Na_2$ and TMT-$Na_3$ and their characteristics and solubility in water.

Aqueous solutions of TMT-$Na_3$ are commercially available and are used for separating heavy metal from the flue gas wash water of garbage incinerators, waste water in the mining industry and in galvanotechnical and chemical plants. The commercially available, aqueous TMT-$NA_3$ solution has a concentration of 15% by weight (Publication TMT 15 of the Degussa company, 3/1986). The saturation concentration of TMT-$Na_3$ in water is approximately 16% by weight at 0° C. and approximately 25% by weight at 20° C. Therefore, although the solubility of TMT-$Na_3$ increases as the temperature rises - from approximately 0.78 mole TMT-$Na_3$ per liter of $H_2O$ at 0° C. to approximately 1.37 mole TMT-$Na_3$ per liter of $H_2O$ at 20° C. - only a solution of approximately 15% by weight has been practical in a commercially available pre-dissolved form. During storage at temperatures of about or even below 0° C., TMT-$Na_3$ crystallizes if the concentration is higher. Such a crystallization makes it considerably more difficult to handle the product. If heat-insulated or heated transport and storage containers were used, TMT-$Na_3$ solutions with a higher concentration could be considered as a commercially supplied form of this product; however, this would make the product and its use more expensive.

TMT-$Na_3$ has also been obtained as a crystalline nonahydrate by reacting cyanuric chloride with NaHS, $Na_2S$ or a NaHS/$Na_2S$ mixture in aqueous medium, adjusting the pH to values of preferably around 12.5 and crystallization - see Published German Patent Application DE-OS 37 29 029. In principle, aqueous solutions of TMT-$Na_3$ can be prepared from crystalline TMT-$Na_3$ nonahydrate at the time of use by dissolving in water; however, it is preferred to have a commercially available pre-dissolved form of TMT-$Na_3$. For this reason, it would be desirable to be able to supply a solution of TMT-$Na_3$ at a concentration of above 15% by weight. The actual active substance is the trimercapto-s-triazine, because it furnishes, together with the heavy metals, slightly soluble compounds which can be readily separated from waste water. Whether trimercapto-s-triazine is used as a solution containing TMT-Na or TMT-$Na_3$ is of lesser importance, since the precipitation pH which is optimum for the recovery of particular metals is generally adjusted in the waste water.

SUMMARY OF THE INVENTION

The object of the present invention is to provide aqueous solutions of sodium salts of trimercapto-s-triazine which have a higher concentration of active substance than current commercially available solutions. Increasing the concentration makes possible a reduction in transportation and storage costs. The solutions should be stable in storage, that is, no crystallization of the active substance or of its salt should occur during storage. The desired concentration depends on the lowest storage temperatures likely to occur in the region where the solutions will be stored. Another problem concerns the preparation of the solutions and their use.

It was found that the solubility of TMT-$H_3$ exhibits a maximum at pH'es around 10.5 to 11. The titration curve of TMT-$H_3$ exhibits a first jump at a pH around 7, a second jump at a pH around 10.5 and a third jump at a pH around 12.5. In the sequence named, the jump are to be associated with the salts TMT-Na, TMT-$Na_2$ and TMT-$Na_3$. While TMT-$H_3$ is practically insoluble in water (less than 0.5% by weight) and TMT-Na is slightly soluble in water (approximately 3% by weight), TMT-$Na_3$ exhibits good solubility, which was to be expected. It could not have been expected that the solubility of TMT-$Na_2$ is considerably above that of the readily soluble TMT-$Na_3$, as was found TMT-$Na_2$ was cited by formula in DE-PS 22 40 549; however, neither a method of preparation of nor prperties of TMT-$Na_2$ have been disclosed hitherto, and its unusually high water solubility also has not been disclosed.

Thus, the present invention provides aqueous solutions of sodium salts of trimercapto-s-triazine whose molar saturation concentration of trimercapto-s-triazine sodium salts at a temperature in a range of 0° C. to 25° C. is above that of the saturation concentration of trimercapto-s-triazine trisodium salt at a given temperature, which are characterized in that more than two but less than three hydrogen atoms of the trimercapto-s-triazine are replaced by sodium ions. That is, the number of sodium ions per mole of trimercaptotriazine in the aqueous solutions is above two and below three.

In order to further describe the invention, the following table gives solubility ranges of TMT-Na salts and salt mixtures. In the table, solubilities are given for compositions in which, respectively, 2.0 –2.2 and 2.6 –2.7 hydrogen atoms are replaced with sodium atoms. That is, in each case, more than 2 hydrogen atoms of the TMT-$H_3$ are replaced. For comparison, solubilities are given for a composition position in which all three hydrogen atoms are replaced with sodium atoms, which corresponds to TMT-$Na_3$. The data shows that the molar saturation concentrations of the solutions according to the invention - moles TMT salt per 1 water - is considerably above the saturation concentration of TMT-$Na_3$.

|  | Number of Na ions per mole trimercapto-s-triazine | Solubility of the TMT-Na salt/-salt mixture (mole TMT salt/1 $H_2O$) | |
| --- | --- | --- | --- |
|  |  | 0° C. | 20° C. |
| According to the invention | 2.0–2.2 | 1.9–2.2 | 2.9–3.2 |
|  | 2.6–2.7 | 1.5–1.6 | 2.0–2.2 |
| State of the art | 3.0 | 0.78 | 1.37 |

If, e.g., 2.2 hydrogen atoms are replaced in the trimercapto-s-triazine by Na ions, this corresponds to a salt mixture of 80 mole % TMT-$NA_2$ and 20 mole % TMT-$Na_3$. Surprisingly, even salt mixtures of approximately 70 mole % TMT-$NA_3$ and 30 mole % TMT-$Na_2$ exhibit a high water solubility, namely, approximately 1.5 moles/liter $H_2O$ at 0° C. and approximately 2.0 moles/liter $H_2O$ at 20° C.

If less than 2 hydrogen atoms of trimercapto-s-triazine are replaced by Na ions, TMT-Na precipitates. In order to reliably avoid a turbidity by TMT-Na in the solutions of the invention, more than 2 hydrogen atoms of the TMT-$H_3$ should be replaced by Na ions. It is especially preferable if more than 2 and up to 2.2 hydrogen atoms of the TMT-$H_3$ are replaced by Na ions since solutions which are stable in storage and have the highest concentration are obtained at this ratio. Such concentrated solutions can be used as a preferred supply form for the active substance trimercapto-s-triazine because of the associated cost savings for transportation and storage. The solubility of the preferred salt mixtures - TMT-$Na_2$ and little TMT-$Na_3$ - can be more than twice as high as that of TMT-$Na_3$, which had been previously assumed to have the highest solubility of the three TMT-Na salts.

In order to be able to assure storage stability in a reliable manner, the concentration of the supply form is selected in such a manner that it is generally approximately 5%–1% (relative) less than the saturation concentration at the expected lowest storage temperature/transport temperature. An especially preferred, stable supply form contains essentially TMT-$Na_2$ in addition to very little TMT-$Na_3$ and has a concentration of approximately 28% by weight (calculated as TMT-$Na_2$).

Aqueous solutions which contain essentially TMT-$Na_2$ in the concentration of the invention achieve important cost savings during storage and transport. In addition, such solutions are less dangerous because of reduced alkalinity. A further advantage is the fact that there is a lower accumulation of neutral salt when using such solutions for the precipitation of heavy metal in comparison to TMT-$Na_3$ solutions.

The solutions of the invention can be prepared in a known manner by reacting TMT-$H_3$ or TMT-Na with the appropriate amount of sodium hydroxide solution. More specifically, the solutions of sodium salts of trimercapto-s-triazine in accordance with the invention are obtained by reacting trimercapto-s-triazine trisodium salt in the form of a concentrated aqueous solution, or a suspension of the nonahydrate of trimercapto-s-triazine trisodium salt, with trimercapto-s-triazine in a molar ratio of 1:greater than 0 - less than 0.5. The desired concentration for the final solution is set, to the extent necessary, before or after the reaction, by the addition of water.

TMT-$Na_3$ is preferably reacted with TMT-$H_3$ in a molar ratio in a range of 1:0.1 to 1:less than 0.5 in aqueous phase; a molar ratio in a range of 1:0.36 to 1:less than 0.5 results in solutions in which more than 2 to 2.2 hydrogen atoms of the TMT-$H_3$ are replaced by Na ions. In the preparation of the solutions, the starting materials can be added to water in crystalline form; however, it is more economical to use filter-moist TMT-$Na_3$ and filter-moist TMT-$H_3$ if the preparation of these compounds from cyanuric chloride took place in aqueous medium.

Cooling an aqueous solution of TMT-$Na_2$ saturated at 30°–60° C. causes TMT-$Na_2$ to crystallize in the form of a hexahydrate. Filter-moist TMT-$Na_2$ hexahydrate loses residual moisture by evaporation when stored in air until a content of approximately 67% by weight TMT-$Na_2$ along with 33% by weight water of crystallization can be measured in the solid. This product corresponds to TMT-$Na_2.6\ H_2O$.

The hexahydrate of trimercapto-s-triazine disodium salt was just as little known previously as any other solid form of TMT-$Na_2$. The salient property of TMT-$Na_2.6\ H_2O$ is its extraordinarily high solubility in water, which makes its concentrated aqueous solutions especially useful for separating heavy metals from waste waters.

It is possible to produce crystalline TMT-$Na_2.6\ H_2O$ in a comparable manner directly from cyanuric chloride, NaSH and NaOH, as is described for TMT-$Na_3.9\ H_2O$ in DE-OS 37 29 029; however, this is less advantageous. In distinction to TMT-$Na_3.9\ H_2O$, TMT-$Na_2.6\ H_2O$ can not be filtered well, for which reason high residual moisture, which additionally contains sodium chloride from the preparation, remains in the product. Moreover, after the crystallization of TMT-$Na_2.6\ H_2O$ the mother liquor still contains considerable amounts of this salt because of its high water solubility, which must be obtained by precipitation as TMT-$H_3$.

Both the solutions of the invention as well as crystalline TMT-$Na_2.6\ H_2O$ can be obtain in a simple manner and practically free of sodium chloride by means of the changes indicated in the following in the method of preparation for TMT-$Na_3.9\ H_2O$ from cyanuric chloride described in the cited DE-OS 37 29 029.

These changes consist in that, after the conclusion of reaction of cyanuric chloride with NaSH or NaSH-/$Na_2S$ and NaOH, the conditions of crystallization for TMT-$Na_3.9\ H_2O$ are adjusted in such a manner by raising the temperature and/or adding water and/or adjusting to a lower pH, that only a part, preferably approximately two thirds, of the TMT-Na salts formed, crystallize out as TMT-$Na_3.9\ H_2O$. After separation of the salt and an optional washing with water, TMT-$H_3$ is precipitated from the combined filtrates - mother liquor and wash water - by means of the addition of a mineral acid, preferably hydrochloric acid, separated and optionally washed. The moist filter cake TMT-$Na_3.9\ H_2O$ and the moist filter cake TMT-$H_3$ are charged in such an amount in a small amount of water and reacted with one another so that the molar ratio of TMT-Na$_3$/TMT-H$_3$ permits the preparation of the solutions of the invention in the desired concentration. To the extent necessary, the concentration of the solution obtained is adjusted to the desired value by the further addition of water.

The special advantage of this embodiment of the invention for the preparation of the solutions of the invention resides in the fact that only maximum of 33% of the trimercapto-s-triazine formed from cyanuric chloride has to be isolated in an intermediate step as TMT-H$_3$, that the method can be carried out in a simple manner and that solutions are obtained which are free of sodium chloride or at least contain very little of it.

DETAILED DESCRIPTION OF PREFERRED EMBODIMENTS

The invention is illustrated by the following examples.

EXAMPLE 1

172 g 40% by weight aqueous NaSH (1.23 moles) are diluted with 112 ml water. 75 g cyanuric chloride (0.41 mole) and 60 g 50% by weight aqueous NaOH (0.75 mole) are added at 50° C. in such a manner that the pH is maintained between 9.5 and 10.5 and the temperature at 50° C. After the end of the addition, the mixture is agitated 1 hour more at 50° C. and subsequently adjusted to a pH of 12.5 by means of the addition of 39 g 50% by weight aqueous NaOH (0.48 mole). After the mixture has cooled down to 10° C., it is centrifuged and the filter cake washed with 50 ml water on the centrifuge.

The solid weighs 119.2 g and contains 54.1% by weight TMT-Na$_3$ in addition to water and traces of sodium chloride (less than 0.3% by weight). Filtrate and wash water are combined and acidified with 50 g concentrated hydrochloric acid and the TMT-H$_3$, which is precipitated quantitatively, is filtered and washed free of sodium chloride with water. The washed TMT-H$_3$ filter cake weighs 59.0 g and contains 34.3% by weight TMT-H$_3$.

The filter cakes are stirred into 120 ml water. 298 g of a TMT solution are produced in which 0.38 mole TMT-Na salts are dissolved. This corresponds to a yield of 93.3% relative to the cyanuric chloride used. 2.09 atoms of hydrogen of the TMT-H$_3$ are replaced by sodium. This is an approximately 28% by weight TMT-Na$_2$ solution.

EXAMPLE 2

15 g Na$_2$S (0.19 mole) and 48 g NaHS (0.8 mole) are added to 133 ml water in a vessel and 65 g cyanuric chloride (0.35 mole) are added at 40° C. in such a manner that the temperature is maintained. The pH drops at first to 9 and is maintained at this value by means of the simultaneous addition of a 30% by weight aqueous NaOH until all the cyanuric chloride has been added. After one half hour postreaction time, the pH is raised to above 12.5 by adding the remainder of the total of 115 g sodium hydroxide solution (0.86 mole). The workup takes place in a customary manner; however, the mixture is crystallized at 30° C. and the TMT-Na$_3$ is not washed. 101 g filter cake is obtained containing 52.3% by weight TMT-Na$_3$, 1.5% by weight sodium chloride and 46.2% by weight water. Acidifying the mother liquor with concentrated hydrochloric acid yields, after filtration, 45 g filter cake containing 35.2% by weight TMT-H$_3$ and 64.8% by weight water. The TMT-Na$_3$ filter cake and TMT-H$_3$ filter cake are stirred into 98 ml water. 244 g of an aqueous solution of Na salts of TMT-H$_3$ are produced which contains 0.31 mole TMT salts (88.6% yield relative to cyanuric chloride added). 2.1 atoms of hydrogen are replaced by sodium in the TMT and the solution is an approximately 28% by weight TMT-Na$_2$ solution.

EXAMPLE 3

296 g of the solution obtained according to Example 1 are condensed by evaporation in a vacuum at 50° C. until 115 ml water have been distilled off. As the mixture is cooled off to 10° C., solid crystallizes out which is separated by filtration. 129 g solid are isolated which contains 51.5% by weight TMT-Na$_2$ and 48.5% by weight H$_2$O (free H$_2$O and H$_2$O bound as water of crystallization), as well as 51 g filtrate containing 34% by weight TMT-Na$_2$. The disodium salt of trimercapto-s-triazine hexahydrate (TMT-Na$_2$.6 H$_2$O) is obtained by carefully drying the solid in air.

What is claimed is:

1. An aqueous solution of a mixture of sodium salts of trimercapto-s-triazine having a molar saturation concentration of trimercapto-s-triazine sodium salts at a temperature in a range of 0° C. to 40° which is above that of the saturation concentration of trimercapto-s-triazine trisodium salt at that temperature, and the number of sodium ions per mole of trimercapto-s-triazine in the aqueous solution of said mixture is above two and below three.

2. The mixture of sodium salts of claim 1 wherein said number of sodium ions per mole is above 2 and below 2.7.

3. The mixture of claim 2 wherein said number of sodium ions per mole is above 2 and below 2.2.

4. The mixture of claim 2 which contains between 2.0 and 3.2 moles of trimercapto-s-triazine sodium salts at temperature of 20° C. and above.

5. The mixture of claim 3 which contains 2.0 to 2.2 moles of trimercapto-s-triazine sodium salts at temperatures of 20° C. and above.

6. A method of preparing an aqueous solution of a trimercapto-s-triazine sodium salt according to any one of claims 1 to 5 in which trimercapto-s-triazine trisodium salt in the form of a concentrated aqueous solution or an aqueous suspension of the nonahydrate of trimercapto-s-triazine trisodium salt is reacted with trimercapto-s-triazine in a molar ratio of 1:less than 0 - less than 0.5 and the desired concentration is set, to the extent necessary, before or after the reaction, by the addition of water.

7. A method as set forth in claim 6 in which trimercapto-s-triazine trisodium salt nonahydrate and trimercapto-s-triazine are used in a molar ratio of 1 to 0.1 to 1 to less than 0.5 and the amount of water corresponds to that required to achieve the ultimate desired concentration.

* * * * *